US009011925B2

(12) United States Patent
Chou et al.

(10) Patent No.: US 9,011,925 B2
(45) Date of Patent: Apr. 21, 2015

(54) METHOD FOR PREPARING POLYSACCHARIDE NANOCOMPOSITE PARTICLES AND USES OF THE SAME

(75) Inventors: Chih-Wei Chou, Taichung (TW);
Yueh-Hsiung Kuo, Taichung (TW);
Chin-Heng Yang, Taichung (TW)

(73) Assignee: China Medical University, Taichung (TW)

( * ) Notice: Subject to any disclaimer, the term of this patent is extended or adjusted under 35 U.S.C. 154(b) by 0 days.

(21) Appl. No.: 13/282,188

(22) Filed: Oct. 26, 2011

(65) Prior Publication Data
US 2012/0282342 A1    Nov. 8, 2012

(30) Foreign Application Priority Data

May 4, 2011 (TW) .............................. 100115575 A

(51) Int. Cl.
*A61K 9/14* (2006.01)
*A61K 9/51* (2006.01)
*A61K 31/357* (2006.01)

(52) U.S. Cl.
CPC ............. *A61K 9/5161* (2013.01); *A61K 31/357* (2013.01)

(58) Field of Classification Search
CPC ..................................................... A61K 31/357
USPC .......................................... 424/493; 514/464
See application file for complete search history.

(56) References Cited

U.S. PATENT DOCUMENTS 6,306,899 B1 * 10/2001 Cheng et al. .................. 514/464
6,649,192 B2 * 11/2003 Alonso Fernandez et al. .............................. 424/499

OTHER PUBLICATIONS

Chih-Wei Chou, Chia-Heng Yang, Yueh-Hsiung Kuo, Te-Hsing Wu, "Different Herbal-Loaded Chitosan Nanoparticles As Drug Carrier for Colon Cancer Therapy: Sythesis, Characterization and Functionality", 2010 International Symposium of Materials on Regenerative Medicine, Nov. 3-5, 2010.
Honglin Song, Shufang Nie, Xinggang Yang, Ning Li, Hongtao, Xu, Liangyuan Zheng, Weisan Pan, "Characterization and in vivo Evaluation of Novel Lipid-Chlorambucil Nanospheres Prepared Using a Mixture of Emulsifiers for Parenteral Administration", *International Journal of Nanomedicine*, Nov. 8, 2010, pp. 933-942.
Meirong Song, Yanyan Li, Catling Fai, Shumin Cui, Baoan Cui, "The Controlled Release of Tilmicosin from Silica Nanoparticles", *Drug Development and Industrial Pharmacy*, vol. 37, No. 6, 2011, pp. 714-718.

* cited by examiner

*Primary Examiner* — Jake Vu
(74) *Attorney, Agent, or Firm* — Greer, Burns & Crain, Ltd.

(57) ABSTRACT

A method for preparing polysaccharide nanocomposite particles is provided. The method comprises providing a first solution comprising an active component and a polysaccharide; adding a cross-linking agent to the first solution to provide a second solution; and allowing the second solution to conduct the reaction to form polysaccharide nanocomposite particles. The polysaccharide nanocomposite particles thus prepared show good coating ratio and enhanced applicability. Also provided is a method for inducing cancer cell apoptosis in a subject, comprising administrating to the subject an effective amount of the polysaccharide nanocomposite particles.

5 Claims, 3 Drawing Sheets

METHOD FOR PREPARING POLYSACCHARIDE NANOCOMPOSITE PARTICLES AND USES OF THE SAME

CROSS-REFERENCES TO RELATED APPLICATIONS

This application claims the benefit of Taiwan Patent Application No. 100115575, filed on May 4, 2011, in the Taiwan Intellectual Property Office, the disclosure of which is incorporated herein in its entirety by reference.

BACKGROUND OF THE INVENTION

1. Field of the Invention

The present invention relates to a method for preparing polysaccharide nanocomposite particles and its use, and especially relates to a method for preparing polysaccharide nanocomposite particles for inducing cancer cell apoptosis and its use.

2. Descriptions of the Related Art

Nanotechnology is directed to the study of novel physical and chemical properties of various substances on the atomic or molecular scale. Generally, nanomaterials are materials with particle sizes between about 1 to about 100 nanometers, and have advantages of a small size, controllable shape, high ratio of surface area to volume, and high packing density. Nanotechnology has been widely applied to various industries, including traditional industries (such as chemical engineering, material, and energy industries) and high-tech industries (such as electronic, photoelectric, and biomedical material fields).

In the field of biomaterials, nanotechnology is mainly applied in the development of pharmaceutical nanocarriers. Pharmaceutical nanocarriers can improve pharmacokinetics properties, and precisely control drug delivery mechanisms. For example, the toxicity of some medicaments can be significantly reduced by designing and controlling the size and surface properties of pharmaceutical carriers, thereby reducing the adverse effects of the medicaments, and even increasing the bioavailability. In addition, some medicaments have poor water solubility, and the water solubility of these medicaments can be increased when carried by pharmaceutical nanocarriers, which extends the application range of these medicaments accordingly.

Presently, there are many methods for preparing pharmaceutical nanocarriers in different forms, such as nanoparticles, nanoliposomes, solid lipid nanoparticles, pharmaceutical magnetic nanoparticles, etc. However, the steps of conventional methods for preparing pharmaceutical nanocarriers are complicated and have many limitations, and the carrying effect of the resultant nanocarriers is usually unsatisfying.

For example, Song H. et al. combined an oil phase solution with a liquid phase solution, and separated the obtained particles by a high pressure homogenizer to prepare solid lipid nanoparticles. Even though the drug coating ratio of these solid lipid nanoparticles can reach 80%, this method is not applicable to medicaments which are sensitive to shear force. In addition, the emulsifier used in this method may remain in the products, and reduce the purity and quality of the products. This method can be seen in Song H. et al., Characterization and In Vivo Evaluation of Novel Lipid-Chlorambucil Nanospheres Prepared Using a Mixture of Emulsifiers for Parenteral Administration, Int. J. Nanomedicine, 2010, Nov. 9; 5:933-42, which is incorporated hereinto by reference. In addition, there is also a conventional method in which a silica sol is slowly dropped into a tilmicosin antibiotic solution, and the solution is stirred at room temperature for about 20 minutes to obtain nanoparticles. Although this process is simpler, the highest drug coating ratio is merely about 64%, showing a poor carrying effect. This method can be seen in Meirong Song et al., The Controlled Release of Tilmicosin from Silica Nanoparticles, Drug Dev. Ind. Pharm., 2011 Jan. 5, which is incorporated hereinto by reference.

In view of the above, the present invention provides a novel and simple method for preparing polysaccharide nanocomposite particles of an anti-cancer medicament carried by polysaccharides. The nanocomposite particles of the present invention have advantages that include a good coating ratio, high bioavailability, wide applicability, etc.

SUMMARY OF THE INVENTION

The primary objective of this invention is to provide a method for preparing polysaccharide nanocomposite particles, comprising the following steps: providing a first solution comprising an active component and a polysaccharide, wherein the active component is selected from a group consisting of a compound of formula (I) and a pharmaceutically acceptable salt or ester of the compound of formula (I), a compound of formula (II) and a pharmaceutically acceptable salt or ester of the compound of formula (II), and combinations thereof:

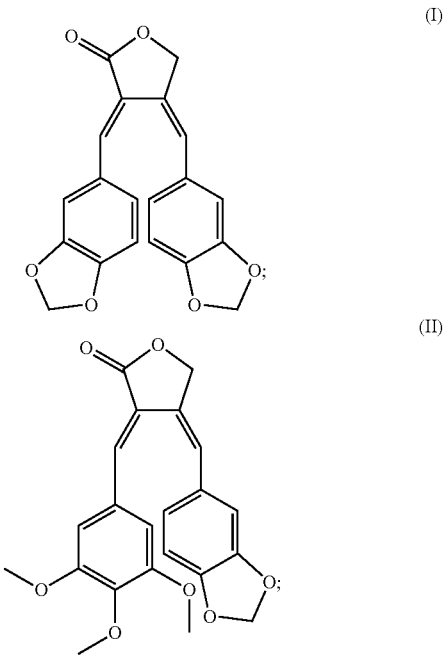

adding a cross-linking agent to the first solution to provide a second solution; and maintaining the second solution at about 20° C. to 80° C. for about 0.5 to 6 hours to form polysaccharide nanocomposite particles; wherein, the molar ratio among the active component, polysaccharide, and cross-linking agent is about 1:1.3-26:4.3-85.

Another objective of this invention is to provide a polysaccharide nanocomposite particle, wherein the particle has a core, comprising the aforesaid active component; and a carrier, derived from a polysaccharide and a cross-linking agent; wherein, the carrier covers at least a part of the surface of the core.

Yet another objective of this invention is to provide a method for inducing cancer cell apoptosis in a subject, comprising administrating to the subject an effective amount of the aforesaid polysaccharide nanocomposite particle.

The detailed technology and preferred embodiments implemented for the subject invention are described in the following paragraphs accompanying the appended drawings for people skilled in this field to well appreciate the features of the claimed invention.

DESCRIPTION OF THE PREFERRED EMBODIMENT

Figure 1:
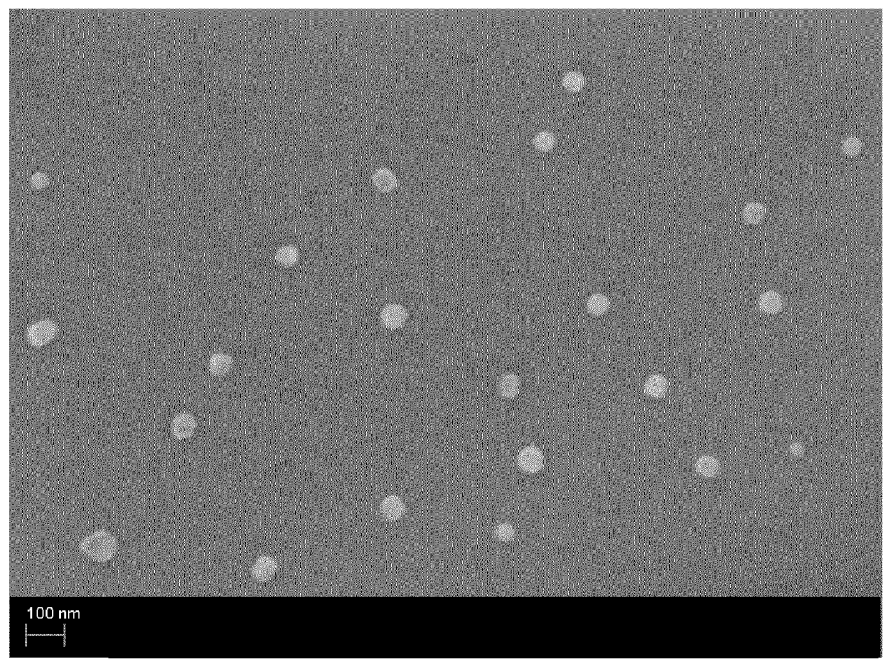
FIG. 1 is an SEM picture showing polysaccharide nanocomposite particles illustrated in Example 1.

The following will describe some embodiments of the present invention in detail. However, without departing from the spirit of the present invention, the present invention may be embodied in various embodiments and should not be limited to the embodiments described in the specification. In addition, unless otherwise stated herein, the terms "a (an)", "the", or the like used in this specification (especially in the claims hereinafter) shall be understood to encompass both the singular form and the plural form. Furthermore, in this specification, the term "coating ratio" means the percentage of the amount of the active component in the prepared polysaccharide nanocomposite particles with respect to the total additive amount of the active component used for the preparation of the nanocompoiste particles as follows.

$$\text{Coating ratio} = 100\% \times \frac{\begin{pmatrix} \text{amount of active component contained in} \\ \text{prepared polysaccharide nanocomposite particles} \end{pmatrix}}{\begin{pmatrix} \text{additive amount of active component used for} \\ \text{preparing polysaccharide nanocomposite particles} \end{pmatrix}}$$

The present invention provides a polysaccharide nanocomposite particle which has a satisfying coating ratio, good dispersibility, biocompatibility and applicability and is easy to preserve by using a simple preparation process, in which polysaccharide is used to carry (or coating) an active component with an anti-cancer effect and low water solubility to increase the water solubility of the active component.

In the method according to the present invention, a first solution comprising an active component and a polysaccharide is first provided. The first solution can be prepared by the following steps.

Dissolving the active component in a first solvent to provide an active component solution, wherein the first solvent can be any solvent suitable for dissolving the active component, including but not limited to dimethyl sulfoxide, methanol, ethanol, and combinations thereof. Preferably, the first solvent is dimethyl sulfoxide.

Dissolving the polysaccharide in a second solvent to provide a polysaccharide solution, wherein the second solvent can be any suitable acidic water solution, including but not limited to acetic acid, hydrochloric acid, and combinations thereof. Preferably, the second solvent is acetic acid.

Mixing the active component solution with the polysaccharide solution. This mixing step usually can be accompanied by stirring, such as by using a rotary stirring machine.

The active component in the first solution can be selected from a group consisting of a compound of formula (I) and a pharmaceutically acceptable salt or ester of the compound of formula (I), a compound of formula (II) and a pharmaceutically acceptable salt or ester of the compound of formula (II), and combinations thereof:

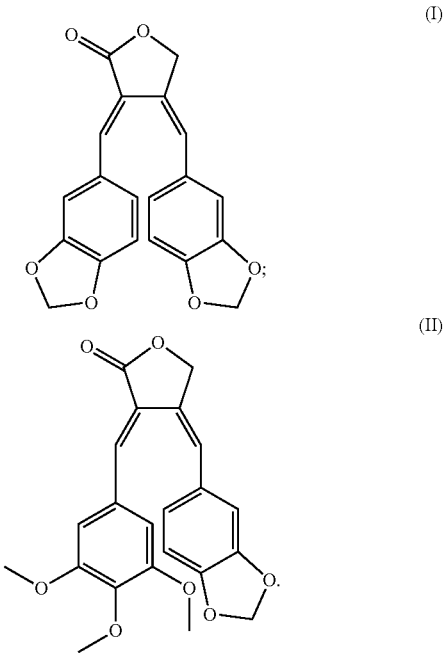

The compound of formula (I) (hereinafter referred to as "KCY-Tai 1") is one of the components extracted from Taiwania cryptomerioides Hayata The compound of formula (II) (hereinafter referred to as "KCY-Tai 2") is a derivative obtained by modifying the chemical structure of KCY-Tai 1. As shown in formula (I) and formula (II), the structures of KCY-Tai 1 and KCY-Tai 2 consist of a plurality of aromatic rings, rendering these compounds hard to be dissolved in water. Thus, organic solvents are required to dissolve them.

In addition, it has been indicated in documents that KCY-Tai 1 and KCY-Tai 2 have the anti-bacteria, anti-mite, anti-termite, and anti-fungus effects. It has also been shown by experiments that KCY-Tai 1 and KCY-Tai 2 have significant cytotoxicity effects on lung cancer cells, breast cancer cells, and rectal cancer cells. In the previous study, the mechanism of KCY-Tai that causes cell apoptosis was analyzed by using a human lung cancer cell line, HepG2/A2, as a cell model. The cell cycle analysis experiment showed that KCY-Tai 1 resulted in a remarkable accumulation of cyclin B1/cdc2 complex with kinase activity in the cells, indicating that the cells were arrested at G2/M phase. Furthermore, the immunofluorescence staining also showed that KCY-Tai 1 can interrupt the formation of mitotic spindle in the cells. In addition, after the cells were treated with KCY-Tai 1, the cells showed micronucleation, DNA fragmentation, and activation of caspase-3, indicating that KCY-Tai 1 could induce cytotoxicity effect by inducing cell apoptosis. In another aspect, the tumor suppressor protein p53 is an important factor related to the regulation of cell growth and apoptosis. The experiment result showed that KCY-Tai 1 treatment could result in the activation of p53 protein in HepG2/A2 cells, and that the cytotoxicity of KCY-Tai 1 could be inhibited when the cells were treated with a p53 protein inhibitor (PFT-a) or the p53 protein expression was inhibited by RNA interference. These results indicated that the cell apoptosis caused by KCY-Tai 1 was regulated via p53 protein.

Because the polysaccharide nanocomposite particle prepared by the method of the present invention comprises the aforesaid active component and/or a pharmaceutically acceptable salt or ester thereof, the particle can be used to induce the apoptosis of cancer cells (such as lung cancer cell, breast cancer cell, rectal cancer cell, etc.).

According to the present invention, the additive amount of the active component usually may influence the particle size and coating ratio of the obtained polysaccharide nanocomposite particles. For example, when the additive amount of the active component is higher, the coating ratio of the obtained polysaccharide nanocomposite particles is higher and the particle size thereof is larger. As a result, in the method of the present invention, the concentration of the active component in the active component solution is usually controlled at about 2 wt/vol % to about 21 wt/vol %; preferably about 4 wt/vol % to about 16 wt/vol %. Herein, the concentration unit "wt/vol %" refers to the weight (in gram) of the active component dissolved in 100 milliliter of the first solvent. For instance, about 2 wt/vol % refers to that there are about 2 grams of the active component dissolved in 100 milliliter of the first solvent.

In the method of the present invention, in addition to the active component, the first solution also comprises a polysaccharide, which is used to carry (or coat) the active component. The polysaccharide suitable for the present invention is composed of monomers selected from a group consisting of glucosamine, N-acetylglucosamine, and a combination thereof, such as a derivative from chitin. Generally, chitin is a high molecular material formed from the polymerization of N-acetylglucosamine monomers. Chitin widely exists in the shell of insects, especially in the shell of crustacean animals. Chitosan is produced by the deacetylation of chitin. In general, the higher the degree of deacetylation, the better the solubility of the obtained chitosan. Chitosan is non-toxic and has high biocompatibility and biodegradability to the human body. It is believed that chitosan has effects of lowering cholesterol and blood pressure, enhancing immunity, hemostasis, anti-bacteria, etc. In addition, chitosan is accessible, and thus, it is widely applied in health food and antibacterial materials. Therefore, in the method of the present invention, it is preferable to use chitosan as a polysaccharide to carry the active component. In general, the viscosity of chitosan is about 20 cP to 2000 cP, and preferably is about 20 cP to 800 cP, and the degree of deacetylation is generally about 75% to about 85%.

The method of the present invention also comprises adding a cross-linking agent to the aforesaid first solution to provide a second solution. The cross-linking agent that can be used in the present invention is selected from a group consisting of tripolyphosphate, sulfate, citrate, glutaraldehyde, and combinations thereof. Preferably, the cross-linking agent is tripolyphosphate, such as sodium tripolyphosphate. According to the method of the present invention, the cross-linking agent can be dissolved in a third solvent (such as ultrapure water) in advance to form a cross-linking agent solution, which is then added into the first solution. Preferably, the cross-linking agent solution is dropped into the first solution at a constant rate under stirring, for example, by using a rotary stirring machine to evenly mix the active component, polysaccharide, and cross-linking agent in the solution.

After the aforesaid second solution is obtained, a reaction is carried out, preferably under stirring (e.g., using a rotary stirring machine), in which the polysaccharide reacts with the cross-linking agent in the solution, and carries (or coats) the active component to form the desired polysaccharide nanocomposite particles. Without being limited by theories, for instance, when chitosan is used as the polysaccharide, as chitosan is dissolved in a solvent (such as acetic acid), the $NH_2$ groups on the surface of chitosan are protonated to form $NH_3^+$ ions with positive charges. After the solvent is mixed with a cross-linking agent (such as tripolyphosphate), the electrostatic interaction between $NH_3^+$ ions and anions (such as $P_3O_{10}^{5-}$) formed after the dissociation of the cross-linking agent is generated, and a complexation reaction occurs to form chitosan particles. The obtained particles can carry the active component to provide desired nanocomposite particles.

In view of the above, the amount of polysaccharide and the cross-linking agent also can be used to adjust the yield and coating ratio of the obtained polysaccharide nanocomposite particles. For example, when the amount of the polysaccharide or the cross-linking agent is too low, the yield of polysaccharide nanocomposite particles may decrease, and even particles cannot be formed. In addition, the obtained polysaccharide nanocomposite particles may have a poor coating property. Thus, it is not economically beneficial. On the contrary, when the amount of the polysaccharide or the cross-linking agent is too high, the particle size of the obtained polysaccharide nanocomposite particles may become too large due to excessively high cross-linking, resulting in aggregation. As a result, in the method of the present invention, the concentration of polysaccharide in the first solution is usually controlled at about 0.05 wt/vol % to about 2.5 wt/vol %, and preferably at about 0.5 wt/vol % to about 1.5 wt/vol %. Herein, the concentration unit "wt/vol %" refers to the weight (in gram) of polysaccharide dissolved in 100 milliliters of the first solution. The concentration of the cross-linking agent in the cross-linking agent solution is usually controlled at about 0.1 wt/vol % to about 1.5 wt/vol %, preferably at about 0.3 wt/vol % to about 0.9 wt/vol %. Herein, the concentration unit "wt/vol %" refers to the weight (in gram) of the cross-linking agent dissolved in 100 milliliters of the third solvent.

In addition, according to the method of the present invention, the second solution is maintained at about 20° C. to 80° C., and preferably at about 20° C. to 40° C., to conduct the reaction. The reaction is usually carried out for about 0.5 to 6 hours, and preferably for about 2 hours to 4 hours. If the reaction temperature is too low or the reaction time is too short, the reaction rate may be too slow, or the reaction may be incomplete, causing low yield and poor coating performance of the polysaccharide nanocomposite particles. If the reaction temperature is too high, it may cause a bad influence on the efficacy of the active component. Moreover, if the reaction time is too long, it may result in the over-reaction of the cross-linking agent, thus, enlarging the particle size of the polysaccharide nanocomposite particles and causing the aggregation of the particles.

In the present invention, in view of the production cost and the influence of the amounts of the active component, polysaccharide, and cross-linking agent on such as particle size, degree of cross-linking, coating ratio, etc., the molar ratio among the active component, polysaccharide, and cross-linking agent is about 1:1.3-26:4.3-85. For example, when the compound of formula (I) is used as the active component, the molar ratio among the active component, polysaccharide, and cross-linking agent is about 1:1.3-21:4.3-69, and preferably about 1:1.8-6:6.2-20. When the compound of formula (II) is used as the active component, the molar ratio among the active component, polysaccharide, and cross-linking agent is about 1:1.6-26:5.3-85, and preferably about 1:2.2-11.5:7.5-37.5.

In the method of the present invention, when the reaction of the second solution is finished, the solvent and un-reacted substances can be optionally removed by using any suitable approach. For instance, when the reaction is finished, the second solution can be treated by centrifugation. For example, the second solution can be centrifuged at about 10,000 rpm to about 20,000 rpm under low temperature (about 0° C. to 10° C.) for about 10 to 60 minutes. Then, the supernatant is discarded, and the precipitate (comprising the polysaccharide nanocomposite particles obtained from the reaction) is kept. Afterwards, the precipitate can be washed by ultrapure water, and the centrifugation step is performed again and can be optionally repeated twice or more to increase the purity of the obtained particles. Eventually, the obtained polysaccharide nanocomposite particles are optionally separated with water (preferably with ultrapure water) to preserve the particles in the form of a dispersion solution.

The present invention also provides a polysaccharide nanocomposite particle, which can be prepared by the method as described above. The nanocomposite particle comprises a core and a carrier, wherein the carrier covers at least a part of the surface of the core. According to the polysaccharide nanocomposite particle of the present invention, the core and carrier can be contained in the polysaccharide nanocomposite particle in any suitable manner. For example, the carrier can completely or partially cover the surface of the core, wherein the surface of the carrier may be also attached with the active component.

In the present invention, the core of the polysaccharide nanocomposite particle comprises an active component selected from a group consisting of the compound of formula (I) and a pharmaceutically acceptable salt or ester of the compound of formula (I), the compound of formula (II) and a pharmaceutically acceptable salt or ester of the compound of formula (II), and combinations thereof. The carrier of the polysaccharide nanocomposite particle is derived from a polysaccharide and a cross-linking agent. Herein, the phrase "the carrier is derived from a polysaccharide and a cross-linking agent" means that the carrier is formed by the reaction between the polysaccharide and cross-linking agent. The polysaccharide is composed of monomers selected from a group consisting of glucosamine, N-acetylglucosamine, and a combination thereof. Preferably, the polysaccharide is a derivative of chitin, such as chitosan. The cross-linking agent is selected from a group consisting of tripolyphosphate, sulfate, citrate, glutaraldehyde, and combinations thereof. Preferably, the cross-linking agent is tripolyphosphate, such as sodium tripolyphosphate.

The polysaccharide nanocomposite particle according to the present invention has a coating ratio of at least about 65%, preferably at least about 85%, and more preferably at least about 95%. This coating ratio shows a satisfying coating property. In addition, the applicability of the composite particle of the present invention is increased by using polysaccharides. For example, the water solubility, biocompatibility, etc. of the composite particle are improved.

Because the active component, KCY-Tai 1 and KCY-Tai 2, used in the present invention has the effect of inducing cancer cell apoptosis, the present invention also provides a method for inducing cancer cell apoptosis in a subject, comprising administrating to the subject an effective amount of the polysaccharide nanocomposite particle of the present invention. Based on the known activity of KCY-Tai 1, the method of the present invention can be used for increasing the expression level of p53 protein in cancer cells, and especially can be used for increasing the expression level of p53 protein in lung cancer cells, breast cancer cells, or rectum cancer cells. Specifically, the method of the present invention can be used for interrupting the formation of mitotic spindle, arresting the cell cycle at G2/M phase, and blocking cell cycle progression in cancer cells.

The present invention will be further illustrated with reference to the following examples. However, these examples are only provided for illustration purposes, but not to limit the scope of the present invention. It is obvious to those skilled in the art that various changes and modifications can be made in the technical spirit of the present invention, and thus, it is apparent that these changes and modifications are included within the scope of the appended claims and their equivalents. The experiment methods and instruments are described as follows.

[Calculation of the Coating Ratio of the Active Component]

The stock solutions of the active component of the compound (I) (i.e., active component (I)) and the compound (II) (i.e., active component (II)) were respectively diluted to 10, 20, 40, 80, 100, and 200 ppm. The absorbance of the diluted samples was determined by using an UV-Vis spectrophotometer (UV-1700, SHIMADZU, Japan) under the wavelengths of 288 nm (for active component (I)) and 276 nm (for active component (II)) to obtain a calibration curve. Then, the absorbance of the supernatant of the polysaccharide nanocomposite particles was determined under these wavelengths to analyze the amount of the un-coated active component. The coating ratio of the active component was calculated by the following formula:

$$\text{Coating ratio } \% = 100\% \times \left(\frac{\text{amount of active component contained in prepared polysaccharide nanocomposite particles}}{\text{additive amount of active component used for preparing polysaccharide nanocomposite particles}}\right) =$$

$$100\% \times \left[\frac{\left(\begin{array}{c}\text{the total additive amount of the active component} - \\ \text{the amount of the un-coated active component}\end{array}\right)}{\text{the total additive amount of the active component}}\right]$$

[Particle Size Analysis]

The samples were put into an ultrasonic vibration machine to vibrate for 2 hours to uniformly separate the particles. Then, the appropriate amount of the samples was dropped on a silicon chip and put in an oven to be dried. The surface morphology of the samples was observed by a field emission scanning electron microscopy (SEM, Jsm-6700F Oxford Inca Energy 400, Jeol, Japan).

[Surface Potential Analysis]

The samples were diluted 50-folds with water, and sonicated for 1 hour by using an ultrasonic vibration machine. Then, the samples dissolved in water were analyzed by using a Zetasizer machine (Malvern ZS90) based on the principle of dynamic light scattering (DLS) to observe the surface potential and particle size distribution of the particles.

[Cytotoxicity Assay]

Colo 205 human rectum tumor cells were inoculated in a 24-well culture dish ($1 \times 10^4$ cells/well), and incubated in an incubator at 37° C. under 5% $CO_2$ for 24 hours. Then, the active component (KCY-Tai 1 and KCY-Tai 2) or polysaccharide nanocomposite particles (KCY-Tai 1-CNPs and KCY-Tai 2-CNPs 2) with different concentrations (0.39 to 12.5 μg/ml) was respectively added into the culture dish, and the cells were incubated for 24, 72, and 120 hours. The cells were washed with 1×PBS twice. MTT (3-(4,5-dimethyl thiazole-2-yl)-2,5-diphenyl tetrazolium bromide) (0.5 mg/ml) was added to the culture dish (200 μl/well), and the dish was placed in an incubator at 37° C. under 5% $CO_2$. After incubating for 4 hours, MTT was sucked out and removed, and 500 ml dimethyl sulfoxide (DMSO) was added into each well. After incubating on the shaker for 30 minutes, 200 μA of the sample was sucked out from each well and transferred into a 96-well culture dish. The absorbance of the sample was determined under the wavelength of 570 nm by an enzyme-linked immunosorbent assay (ELISA) reader.

[UV-Vis Spectrum Analysis]

The absorption spectra of the active component (KCY-Tai 1, KCY-Tai 2, and active components carried by polysaccharide) were determined by an UV-Vis spectrophotometer (UV-1700, SHIMADZU, Japan) under the wavelength from 200 to 800 nm. The absorbance values of the samples under the wavelengths of 288 nm (for active component (I)) and 276 nm (for active component (II)) were analyzed.

EXAMPLE

Preparation of Polysaccharide Nanocomposite Particles

Examples 1 to 6

(1) An electronic balance was used to measure 140 mg KCY-Tai 1 powder, and the powder was dissolved in 14 ml dimethyl sulfoxide to form a 10 wt/vol % KCY-Tai 1 solution.

(2) The electronic balance was used to measure sodium tripolyphosphate powder, and the powder was dissolved in ultrapure water to form a 0.5 wt/vol % sodium tripolyphosphate solution.

(3) The electronic balance was used to measure 0.4 g chitosan (degree of deacetylation: 75 to 85%; viscosity: 20 to 200 cp), and then was dissolved in an acetic acid solution (the amount of acetic acid and ultrapure water is shown in Table 1) to form a chitosan solution.

(4) The KCY-Tai 1 solution prepared in step (1) was added into the chitosan solution prepared in step (3) according to the amount shown in Table 1. The solution was stirred by a rotary stirring machine to obtain a uniform solution. Then, the sodium tripolyphosphate solution prepared in step (2) was added into the uniform solution at a constant rate, and the solution was stirred using a rotary stirring machine at 25° C. for about 3 hours.

(5) The solution obtained from step (4) was centrifuged at 15,500 rpm under 4° C. for about 30 minutes. The supernatant was discarded and the pellet was separated by rinsing with ultrapure water. Then, the sample was centrifuged under the same condition for about 15 minutes, and the supernatant was discarded. The pellet was separated by rinsing with ultrapure water again and stored.

TABLE 1

|  | Ex. 1 | Ex. 2 | Ex. 3 | Ex. 4 | Ex. 5 | Ex. 6 |
|---|---|---|---|---|---|---|
| Acetic acid (ml) | 0.6 | 0.6 | 0.6 | 0.6 | 0.6 | 0.6 |
| Ultrapure water (ml) | 39.295 | 39.19 | 38.98 | 38.56 | 38.14 | 37.72 |
| KCY-Tai 1 solution (ml) | 0.105 | 0.21 | 0.42 | 0.84 | 1.26 | 1.68 |
| Sodium tripolyphosphate solution (ml) | 16 | 16 | 16 | 16 | 16 | 16 |

Examples 7 to 9

Polysaccharide nanocomposite particles were prepared by the same method as Examples 1 to 6, but in step (1), the electronic balance was used to measure 56 mg KCY-Tai 2 powder, and the powder was dissolved in 14 ml dimethyl sulfoxide to form a 4 wt/vol % KCY-Tai 2 solution. The components and amount used are shown in Table 2.

TABLE 2

|  | Ex. 7 | Ex. 8 | Ex. 9 |
|---|---|---|---|
| Acetic acid (ml) | 0.6 | 0.6 | 0.6 |
| Ultrapure water (ml) | 38.35 | 37.3 | 35.2 |
| KCY-Tai 2 solution (ml) | 1.05 | 2.1 | 4.2 |
| Sodium tripolyphosphate solution (ml) | 16 | 16 | 16 |

Figure 2:
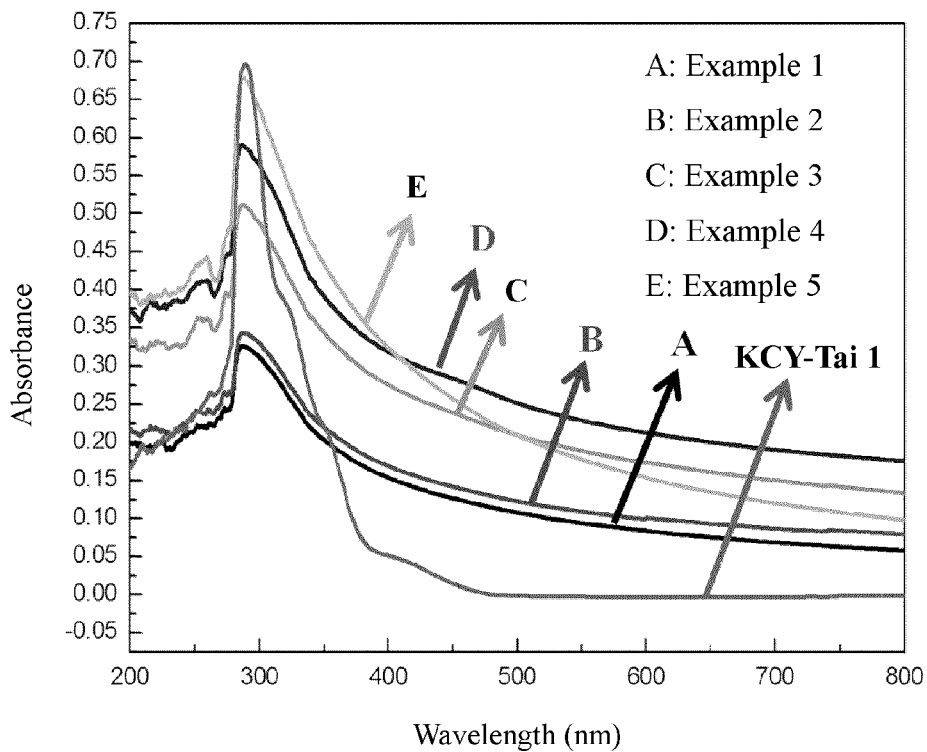
FIG. 2 is an UV-Vis spectrum of KCY-Tai 1 and polysaccharide nanocomposite particles illustrated in Examples 1 to 5.
Figure 3:
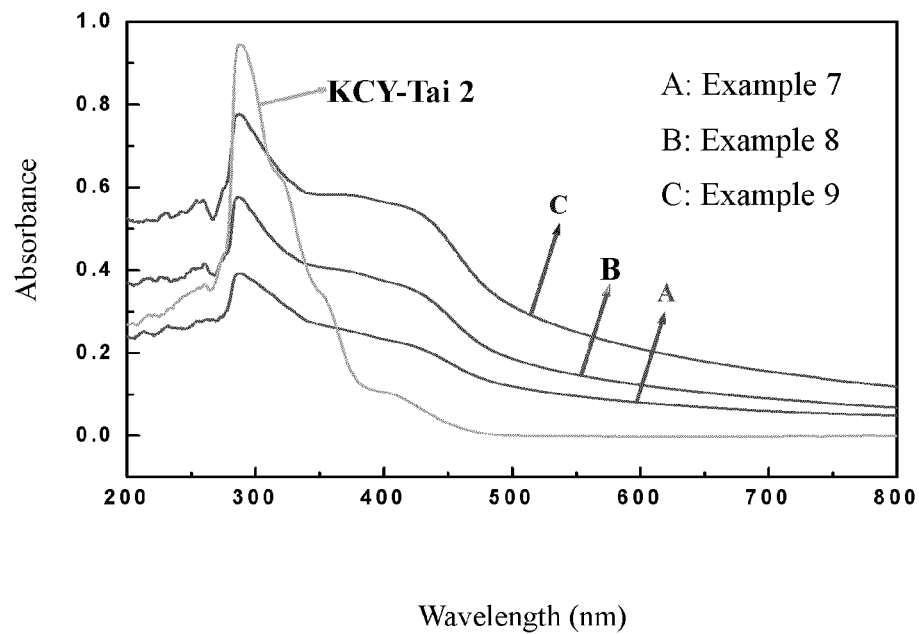
FIG. 3 is an UV-Vis spectrum of KCY-Tai 2 and polysaccharide nanocomposite particles illustrated in Examples 7 to 9.
Figure 4:
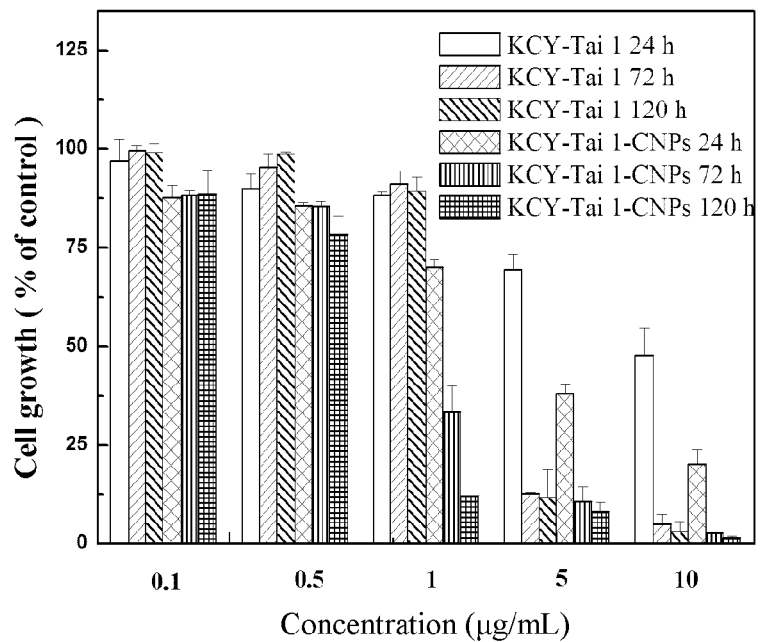
FIG. 4 is a column diagram showing the cytotoxicity assay results of KCY-Tai 1 and polysaccharide nanocomposite particles illustrated in Example 3.
Figure 5:
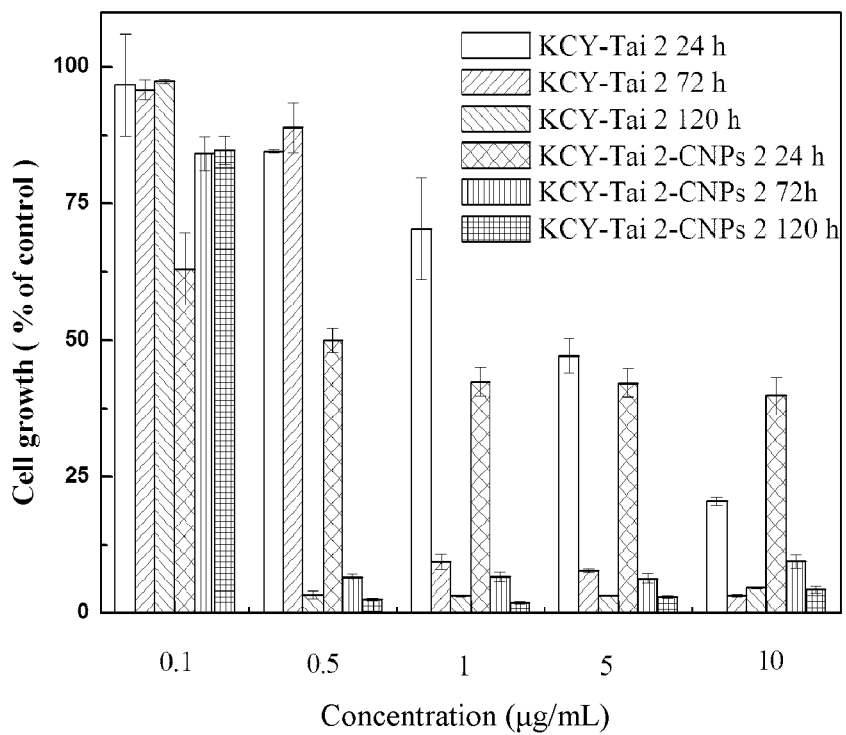
FIG. 5 is a column diagram showing the cytotoxicity assay results of KCY-Tai 2 and polysaccharide nanocomposite particles illustrated in Example 7.

The surface potential of KCY-Tai 1 and KCY-Tai 2 and the coating ratio, drug content, surface potential of the polysaccharide nanocomposite particles of Examples 1 to 9 were measured according to the aforesaid methods. The results are shown in Table 3. The picture of SEM is shown in FIG. 1 (Example 1). The results of UV-Vis spectra are shown in FIGS. 2 and 3. The results of the cytotoxicity assay are shown in FIGS. 4 and 5.

TABLE 3

|  | Coating ratio (%) | Drug content (mg/ml) | Surface potential (mV) |
|---|---|---|---|
| KCY-Tai 1 |  |  | −22.5 |
| Ex. 1 | 65.92 | 0.049229 | 64.7 |
| Ex. 2 | 86.90 | 0.120854 | 61.3 |
| Ex. 3 | 91.84 | 0.259925 | 56.9 |
| Ex. 4 | 96.04 | 0.564941 | 51.7 |
| Ex. 5 | 94.15 | 1.203134 | 48.8 |
| Ex. 6 | 96.31 | 1.641078 | 48.0 |
| KCY-Tai 2 |  |  | −11.8 |
| Ex. 7 | 75.48 | 0.203738 | 57.9 |
| Ex. 8 | 86.3 | 0.717743 | 51.5 |
| Ex. 9 | 90.92 | 1.689534 | 48.9 |

As shown in Table 3 and FIG. 1, the polysaccharide nanocomposite particles according to the present invention showed good coating ratio. The highest coating ratio can reach about 96%. When the concentration of the active component was raised, the coating ratio also increased accordingly. In addition, the molecular surface of chitosan has positive charges, while the molecular surface of the active component, KCY-Tai 1 and KCY-Tai 2, has negative charges, and thus, when KCY-Tai 1 and KCY-Tai 2 bind with chitosan, the surface potential of the particles rises. Therefore, the surface potential of the polysaccharide nanocomposite particles can be measured to determine if the active component is coated. The results of the surface potential analysis in Table 3 indicate that the polysaccharide nanocomposite particles prepared by the method of the present invention have good coating ratio. Therefore, the method of the present invention can decrease drug production cost and significantly simplify the preparation process.

FIGS. 2 and 3 show the UV-Vis spectra of the active component KCY-Tai 1, KCY-Tai 2, and the polysaccharide nanocomposite particles according to the present invention (Examples 1 to 5 and Examples 7 to 9). The results indicate that KCY-Tai 1 and KCY-Tai 2 have remarkable absorption peaks at the wavelengths of 288 nm and 276 nm, respectively. After these active components were coated, the absorption peaks were unchanged, indicating that after these active components were coated by polysaccharide, the chemical structures of these active components were unchanged. If the chemical structures of these active components were changed after they were coated, the efficacy of the medicament will be affected. The above results also indicate that when the coating ratio of polysaccharide increased, the absorbance of the polysaccharide nanocomposite particles at the wavelengths of 288 nm (for active component KCY-Tai 1) and 276 nm (for active component KCY-Tai 2) increased accordingly.

FIGS. 4 and 5 show the results of the cytotoxicity assay of the active component KCY-Tai 1, KCY-Tai 2, and the polysaccharide nanocomposite particles according to the present invention (Examples 3 and 7). The results indicate that when the active component, KCY-Tai 1 and KCY-Tai 2, was coated by polysaccharides, the inhibition effect of these active components on colo 205 human rectum tumor cells was significantly increased. The 1050 (50% concentration of inhibition) of the active component KCY-Tai 1 at the $72^{th}$ hour was increased from 3 μg/ml to 0.8 μg/ml. The 1050 of active component KCY-Tai 2 at the $72^{th}$ hour was increased from 0.7 μg/ml to 0.25 μg/ml. The above results indicate that when KCY-Tai 1 and KCY-Tai 2 were coated by polysaccharide, the active components were protected by polysaccharide, the water solubility of the active components was increased, and the size thereof was uniform. Therefore, the anti-cancer effect of the coated active component is significantly higher than the un-coated active component.

What is claimed is:

1. A method for inducing cancer cell apoptosis in a subject as needed thereof, comprising administering to the subject an effective amount of a polysaccharide nanocomposite particle, wherein the polysaccharide nanocomposite particle comprises:

a core, comprising an active component selected from the group consisting of a compound of formula (I) and a pharmaceutically acceptable salt or ester of the compound, a compound of formula (II) and a pharmaceutically acceptable salt or ester of the compound, and combinations thereof:

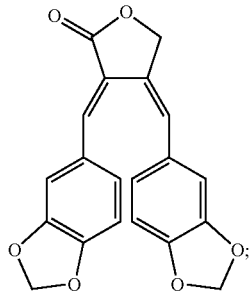

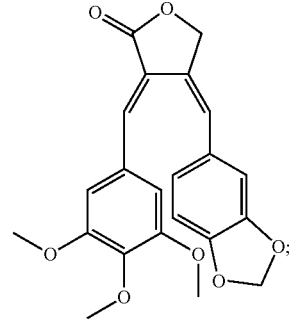

and a carrier, derived from a polysaccharide and a cross-linking agent;

wherein the carrier covers at least a part of the surface of the core; and wherein when the active component is a compound of formula (I) and/or its pharmaceutically acceptable salt or ester, the cancer cells are lung cancer cells, breast cancer cells, or rectum cancer cells.

2. The method as claimed in claim 1, wherein the polysaccharide is composed of monomers selected from the group consisting of glucosamine, N-acetylglucosamine, and combinations thereof; and the cross-linking agent is selected from the group consisting of tripolyphosphate, sulfate, citrate, glutaraldehyde, and combinations thereof.

3. The method as claimed in claim 2, wherein the polysaccharide is chitosan, and the cross-linking agent is tripolyphosphate.

4. The method as claimed in claim 1, wherein the polysaccharide nanocomposite particle is prepared by the following method:

providing a first solution comprising an active component and a polysaccharide, wherein the active component is selected from the group consisting of a compound of formula (I) and a pharmaceutically acceptable salt or ester of the compound, a compound of formula (II) and a pharmaceutically acceptable salt or ester of the compound, and combinations thereof:

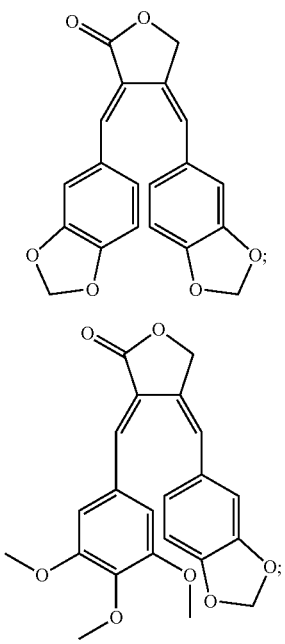

adding a cross-linking agent to the first solution to provide a second solution; and maintaining the second solution at about 20° C. to 80° C. for about 0.5 to 6 hours to form polysaccharide nanocomposite particles;

wherein, the molar ratio between the active component, polysaccharide, and cross-linking agent is about 1:1.3-26:4.3-85.

5. The method as claimed in claim 1, which is used for blocking cell cycle progression in cancer cells.

* * * * *